United States Patent
Kim et al.

(10) Patent No.: US 6,319,229 B1
(45) Date of Patent: Nov. 20, 2001

(54) BALLOON CATHETER AND METHOD OF MANUFACTURE

(75) Inventors: Isaac J. Kim, San Jose; Juan T. Domingo; Celso J. Bagaoisan, both of Union City, all of CA (US)

(73) Assignee: Medtronic PercuSurge, Inc., Sunnyvale, CA (US)

( * ) Notice: Subject to any disclaimer, the term of this patent is extended or adjusted under 35 U.S.C. 154(b) by 0 days.

(21) Appl. No.: 09/432,990

(22) Filed: Nov. 3, 1999

Related U.S. Application Data (62) Division of application No. 09/026,225, filed on Feb. 19, 1998.

(51) Int. Cl.$^7$ .................................................. A61M 29/00
(52) U.S. Cl. ......................... 604/103; 604/96; 604/104; 604/102.01; 606/192; 606/194
(58) Field of Search ............................ 604/96.01, 97.01, 604/98.01, 103, 104, 102.01, 103.01, 103.06; 606/192, 194

(56) References Cited

U.S. PATENT DOCUMENTS

| | | |
|---|---|---|
| 3,144,868 | 8/1964 | Jascalevich . |
| 4,386,179 | 5/1983 | Sterling . |
| 4,445,892 | 5/1984 | Hussein et al. . |
| 4,468,216 | 8/1984 | Muto . |
| 4,490,421 | 12/1984 | Levy . |

(List continued on next page.)

FOREIGN PATENT DOCUMENTS

| | | |
|---|---|---|
| 0 531 117 A2 | 9/1992 | (EP) . |
| 0 577 009 A1 | 6/1993 | (EP) . |
| 0 592 885 A2 | 9/1993 | (EP) . |
| 0 795 340 A2 | 9/1997 | (EP) . |
| WO 95/23619 | 9/1995 | (WO) . |
| WO 96/12516 | 5/1996 | (WO) . |
| WO 96/15824 | 5/1996 | (WO) . |
| WO 97/144084 | 11/1997 | (WO) . |
| WO 98/03218 | 1/1998 | (WO) . |

OTHER PUBLICATIONS

R. Carew, E. Perrin, D. Deisler and E.P. Goldberg, "The Torch", The Newsletter of the Society for Biomaterials, vol. 10, No. 4.

Primary Examiner—Glenn K. Dawson
Assistant Examiner—Jennifer J Maynard
(74) Attorney, Agent, or Firm—Knobbe, Martens, Olson & Bear LLP (57) ABSTRACT

Disclosed herein is a compliant catheter balloon with an improved elastic response and reduced longitudinal expansion, and a method of forming the same. The balloon comprises a SEBS block copolymer, which is longitudinally pre-stretched during the balloon manufacture process. In order to control the working length of a balloon on a catheter, at least one adhesive stop is provided on the catheter which prevents adhesive from wicking into the working length of the balloon. Preferably, a pair of thermoset tubings with an outer diameter size close to the size of the inner diameter of the balloon are inserted on the distal portion of the catheter. After the proper placement of the balloon, the adhesive is applied at the balloon's proximal and distal ends. As the adhesive wicks to the balloon, the thermoset tubings will eventually stop the adhesive to prevent further wicking of adhesive into the balloon's working length. In another aspect of the present invention, there is provided a method of manufacturing a balloon catheter to improve centering of the balloon on the catheter. After a balloon tubing is stretched, the stretched tubing is clamped to a fixture and stabilized at about 100° C. for 15 minutes. This stabilization step ensures that a balloon mounted on a catheter will inflate in a uniform manner.

21 Claims, 2 Drawing Sheets

U.S. PATENT DOCUMENTS

| | | |
|---|---|---|
| 4,511,354 | 4/1985 | Sterling . |
| 4,573,966 | 3/1986 | Weikl et al. . |
| 4,637,396 | 1/1987 | Cook . |
| 4,698,059 | 10/1987 | Johnson . |
| 4,737,219 | 4/1988 | Taller et al. . |
| 4,763,654 | 8/1988 | Jang . |
| 4,820,349 | 4/1989 | Saab . |
| 4,886,496 | 12/1989 | Conoscenti et al. . |
| 4,906,244 | 3/1990 | Pinchuk et al. . |
| 4,946,466 | 8/1990 | Pinchuk et al. . |
| 4,964,409 | 10/1990 | Tremulis . |
| 5,059,178 | 10/1991 | Ya . |
| 5,163,906 | 11/1992 | Ahmadi . |
| 5,167,239 | 12/1992 | Cohen et al. . |
| 5,254,091 | 10/1993 | Aliahmad et al. . |
| 5,256,145 * | 10/1993 | Atkinson et al. .............. 604/96 |
| 5,322,508 | 6/1994 | Viera . |
| 5,423,742 | 6/1995 | Theron . |
| 5,439,000 | 8/1995 | Gunderson et al. . |
| 5,449,343 | 9/1995 | Samson et al. . |
| 5,462,529 | 10/1995 | Simpson et al. . |
| 5,490,838 | 2/1996 | Miller . |
| 5,500,180 | 3/1996 | Anderson et al. . |
| 5,501,667 | 3/1996 | Verduin, Jr. . |
| 5,556,383 | 9/1996 | Wang et al. . |
| 5,558,644 | 9/1996 | Boyd et al. . |
| 5,628,770 * | 5/1997 | Thome et al. .............. 607/101 |
| 5,876,376 * | 3/1999 | Schwab et al. .............. 604/103 |

* cited by examiner

FIG. 1

BALLOON CATHETER AND METHOD OF MANUFACTURE

CROSS-REFERENCE TO RELATED APPLICATION

The present application is a divisional of application Ser. No. 09/026,225, filed Feb. 19, 1998.

BACKGROUND OF THE INVENTION

1. Field of the Invention

The present invention generally relates to medical devices, and in particular, to an improved balloon catheter and method of manufacture.

2. Description of the Related Art

Medical balloon catheters have been proven efficacious in treating a wide variety of blood vessel disorders. Moreover, these types of catheters have permitted clinicians to treat disorders with minimally invasive procedures that, in the past, would have required complex and perhaps life threatening surgeries. For example, balloon angioplasty is now a common procedure to alleviate stenotic lesions (i.e., clogged arteries) in blood vessels, thereby reducing the need for heart bypass operations.

Compliant inflatable balloons, of the type used with medical catheters, increase in diameter with increasing inflation pressure until the balloon burst pressure is reached, as is well-known to those of skill in the art. Such balloons are especially advantageous when used as a medical catheter balloon, or as the securing element of an anchorable guidewire. In both applications, the balloon must be expanded to contact the blood vessel wall. In some treatment procedures, however, the clinician does not know the precise diameter of the blood vessel segment that the balloon must contact. In these situations, the compliant expansion profile of the balloon permits the clinician to make the required contact, by application of increasing inflation pressures to cause increased balloon radial expansion until contact is achieved.

Conventional compliant expansion balloons are generally made of elastomeric materials, such as latex and silicone. Balloons made of these materials utilizing conventional balloon formation techniques suffer from several disadvantages which adversely affect the balloon's performance.

One disadvantage of conventional compliant balloons relates to their elastic response. It is desirable for catheter balloons to have a predictable inflation profile. That is, the balloon should inflate to a certain known size upon application of a specific pressure. Moreover, the balloon should exhibit good elasticity, inflating to approximately the same size upon application of the same specific pressure or volume, even after the balloon has been inflated and deflated multiple times. However, conventional compliant balloons often do not exhibit this desired elastic response, and tend to inflate to larger sizes upon application of the same specific pressure each subsequent time they are inflated. This is because each inflation stretches the balloon, and upon deflation, the balloon does not return to its original deflated size, but instead is somewhat larger. Consequently, upon each subsequent inflation, the stretched balloon inflates to a larger size than before, making it difficult for the clinician to predict the amount of pressure that must be applied to inflate the balloon to the size needed to contact the vessel.

Another disadvantage of conventional compliant balloons relates to their longitudinal expansion. As described previously, compliant balloons tend to increase in radial diameter with increasing inflation pressure. In addition, many compliant expansion balloons also tend to increase in length with increasing inflation pressure. This is an undesirable expansion characteristic, as it creates an unwanted shearing force within the blood vessel, which could lead to vessel trauma.

Accordingly, there exists a need for compliant expansion balloons for use on medical catheters, or as securing members on anchorable guidewires, which have a predictable elastic response, a predictable longitudinal expansion, and a predictable diameter, at different volumes or pressures. In addition, there is a need for methods of making such balloons.

Balloons used for angioplasty and other procedures are bonded to catheter tubular bodies. Conventional balloon bonding techniques used to mount the balloons to catheter tubular bodies include adhesive bonding and heat bonding, as known to those of skill in the art. When adhesive bonding is used, each end of the balloon is mounted to the catheter tubular body to form a fluid tight seal. An adhesive is applied to the ends of the balloon which wicks into the balloon to form a seal with the catheter tube. Typically, clamps are placed adjacent to the working area (i.e., the area within the balloon which is not bonded to the catheter and which is therefore available for inflation) to prevent adhesive flow into the working area. This technique, however, does not provide complete control of the working length because clamps are not completely effective in preventing adhesive flow into the working area. In particular, the difficulty in controlling the clamping force may allow the adhesive to wick into the working area. This creates the problems that the balloon working length may not be at the precise location desired on the catheter tubular body, and that balloon inflation may not be uniform. Thus, there is a need to control adhesive wicking of the balloon seal to control the balloon working length.

A further problem arises from the need to inflate the balloon in a uniform manner. The balloon must be centered around the catheter tube in order to allow a more uniform vessel occlusion or similar effect. Thus, there is also a need for a balloon catheter and a method for manufacturing the same wherein a balloon is centered around a catheter to allow uniform inflation of the balloon.

SUMMARY OF THE INVENTION

The present invention advantageously provides a compliant expansion balloon with an improved elastic response and reduced longitudinal expansion. In one aspect of the present invention, there is provided a longitudinally pre-stretched styrene-ethylene-butylene-styrene (SEBS) compliant catheter balloon. Preferably, the balloon is formed in part by longitudinally stretching an extruded styrene-ethylene-butylene-styrene tube such that the tube increases in length by at least 200%. More preferably, the tube increases in length by at least 600 to 900%. It is also preferred that the balloon be formed from a tube stretched at a rate of from about 10 cm/min to about 30 cm/min. Balloons of this type exhibit decreased longitudinal expansion when inflated. Preferably, the longitudinal expansion of the balloon formed in part by stretching the extruded tube is 20%–50% less than a balloon formed from an unstretched tube of identical composition.

In another aspect of the present invention, there is provided a method of making a compliant inflatable catheter balloon with reduced longitudinal expansion. The first step of the method is to provide an extruded SEBS tube having a first length and a first inner diameter. The extruded SEBS tube is then stretched longitudinally so that the tube forms a second inner diameter smaller than the first diameter, and a second length greater than the first length.

In an alternate first step, there is provided an extruded SEBS tube having a first length and a first thickness. The extruded SEBS tube is then stretched longitudinally so that the tube has a second length greater than the first length, and a second thickness which is less than the first thickness.

After the stretching process, the tube is preferably cut within two hours of the stretching step. In a preferred practice of the method, the second length is at least 600% greater than the first length, more preferably is at least 700% greater than the first length, and optimally is at least 900% greater than the first length.

In addition, it is also preferred that the second diameter be about 40% smaller than the first diameter, more preferably about 30% smaller than the first diameter.

The longitudinal stretching also preferably occurs at a rate of about 10 cm/min–30 cm/min, and takes place in an environment having a temperature of between 0° and 90° C.

In order to control the working length of the balloon on a catheter, at least one adhesive stop is provided on the catheter which prevents adhesive from wicking into the working length of the balloon. Preferably, a pair of thermoset tubings with an outer diameter size close to the size of the inner diameter of the balloon is inserted on the distal portion of the catheter. After the proper placement of the balloon, the adhesive is applied at the balloon's proximal and distal ends. As the adhesive wicks to the balloon, the thermoset tubings will eventually stop the adhesive to prevent further wicking of adhesive into the balloon's working length. So in essence, the thermoset tubings become like a barrier or stopper to control the wicking of adhesive, the seal length and working length all together. This effect not only helps maintain dimensional specifications but also helps to aid in centering the balloon around the catheter.

In one aspect of the present invention, an inflatable balloon catheter is provided comprising an elongate tubular body having proximal and distal ends with a lumen extending through the tubular body from the proximal to the distal end. An inflatable balloon with an interior volume in fluid communication with the lumen is bonded concentrically to the tubular body at its proximal and distal ends by an adhesive. The balloon has a working area within the interior volume which is not bonded to the tubular body. At least one adhesive stop is located on the elongate tubular body and within the interior volume of the balloon to prevent the adhesive from wicking into the working area of the balloon.

In another aspect of the present invention, there is provided a method of manufacturing a balloon catheter to improve centering of the balloon on the catheter. The first step of the method is to extrude a resin to form a tube having an inner and outer diameter and an inner surface. The tube is then pre-stretched to reduce the inner and outer diameters of the tube. The stretched tube is stabilized at a temperature above about 60° C. This stabilization step ensures that a balloon mounted on a catheter will inflate in a uniform manner.

DETAILED DESCRIPTION OF THE PREFERRED EMBODIMENT

Figure 1:
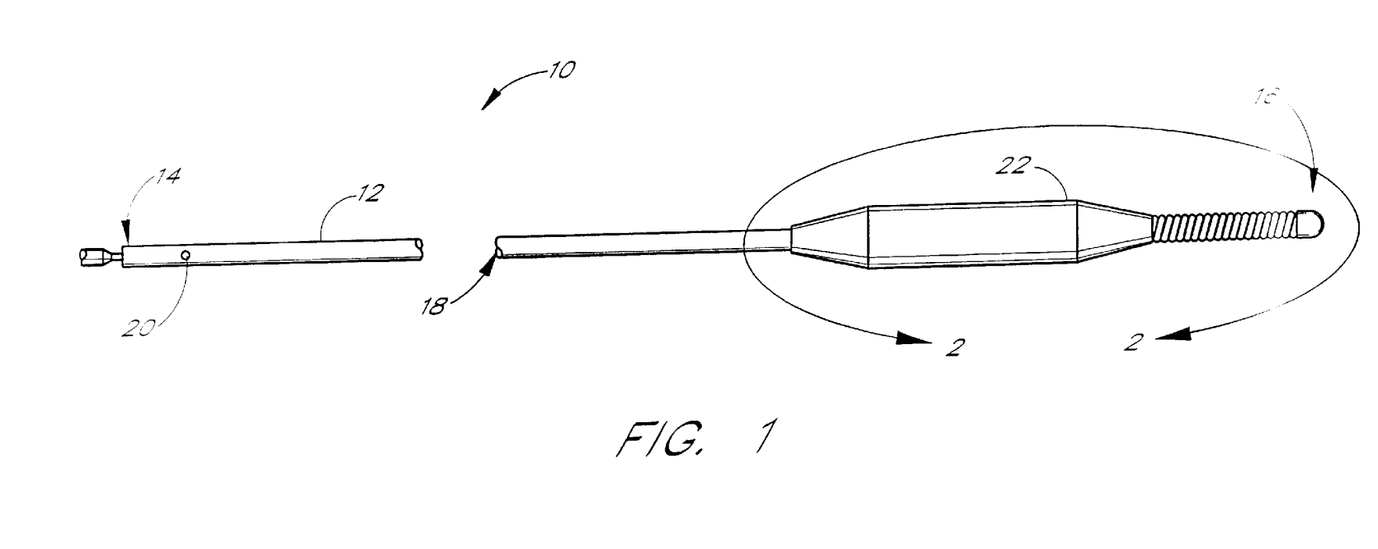
FIG. 1 is a side view of a catheter incorporating the pre-stretched balloon of the present invention.

Referring to FIG. 1, there is depicted a catheter 10 incorporating the balloon of the present invention. Although the balloon of the present invention is depicted and discussed in the context of being mounted on a simple occlusion balloon catheter having a single lumen, it should be appreciated that the present invention is applicable to more complex catheters having structures and functionalities not discussed herein. For example, the present inventors contemplate that the balloon of the present invention may be used on catheters having two or more lumens, such as the main catheter of an emboli containment system. In addition, the balloon of the present invention can be used as the securing member for an anchorable guide wire. Moreover, the present invention is applicable to catheters having other types of balloons, such as dilatation balloons using materials such as polyethylene terephthalate or the like, and other types of catheters, such as irrigation catheters used in drug delivery or radiation therapy. The manner of adapting the balloon of the present invention to these various structures and functionalities will become readily apparent to those of skill in the art in view of the description which follows.

Occlusion Catheter

In the embodiment illustrated in FIG. 1, the balloon of the present invention is mounted on an occlusion balloon catheter 10. Catheter 10 generally comprises an elongate flexible tubular body 12 extending between a proximal control end 14 and a distal functional end 16. Tubular body 12 has a central lumen 18 which extends between ends 14 and 16. An inflation port 20 is provided on tubular body 12 near proximal end 14. Inflation port 20 is in fluid communication with lumen 18, such that fluid passing through inflation port 20 into or out of lumen 18 may be used to inflate or deflate inflatable balloons in communication with lumen 18. Lumen 18 is sealed fluid tight at distal end 16. Inflation port 20 may be similar to existing female luer lock adapters or would be a removable valve at the end, as disclosed in assignee's copending application entitled LOW PROFILE CATHETER VALVE AND INFLATION ADAPTER, application Ser. No. 08/975,723 filed Nov. 20, 1997, the entirety of which is incorporated by reference.

The length of tubular body 12 may be varied considerably depending upon the desired application. For example, where catheter 10 serves as a guidewire for other catheters in a conventional percutaneous transluminal coronary angioplasty procedure involving femoral artery access, tubular body 12 is comprised of a hollow hypotube having a length preferably in the range of from about 160 to about 320 centimeters, with a length of about 180 centimeters being optimal for a single operator device and 300 centimeters for over the wire applications. Alternately, for a different treatment procedure, not requiring as long a length of tubular body 12, shorter lengths of tubular body 12 may be provided.

Tubular body 12 generally has a circular cross-sectional configuration with an outer diameter within the range of from about 0.008 inches to 0.14 inches. Optimally, in most applications where catheter 10 is to be used as a guidewire for other catheters, the outer diameter of tubular body 12 ranges from about 0.010 inches to 0.038 inches, and preferably is about 0.018 inches in outer diameter or smaller.

Larger or smaller sizes of tubular body 12 may also be used. Noncircular cross-sectional configurations of lumen 18 can also be adapted for use with the balloon of the present invention. For example, triangular cross-sectional configurations, rectangular, oval, and other noncircular cross-sectional configurations are also easily incorporated for use with the present invention, as will be appreciated by those of skill in the art.

Tubular body 12 has sufficient structural integrity, or "pushability," to permit catheter 10 to be advanced through vasculature to distal arterial locations without buckling or undesirable kinking of tubular body 12. It is also desirable for tubular body 12 to have the ability to transmit torque, such as in those embodiments where it may be desirable to rotate tubular body 12 after insertion into a patient. A variety of biocompatible materials, known by those of skill in the art to possess these properties and to be suitable for catheter manufacture, may be used to fashion tubular body 12. For example, tubular body 12 may be made of stainless steel, or may be made of polymeric materials such as nylon, polyamide and polyimide or polyethylene or combinations thereof. In one preferred embodiment, the desired properties of structural integrity and torque transmission are achieved by forming tubular body 12 out of an alloy of titanium and nickel, commonly referred to as nitinol. In a more preferred embodiment, the nitinol alloy used to form tubular body 12 is comprised of about 50.8% nickel with the balance being titanium, which is sold under the trade name Tinel (TM) by Memry Corp. It has been found that a catheter tubular body having this composition of nickel and titanium exhibits an improved combination of flexibility and kink resistance in comparison to other materials. Further details are disclosed in assignee's co-pending applications entitled HOLLOW MEDICAL WIRES AND METHODS FOR CONSTRUCTING SAME, application Ser. No. 08/812,876, filed Mar. 6, 1997, and SHAFT FOR MEDICAL CATHETERS application Ser. No. 09/026105, filed on Feb. 19, 1998, both references in their entirety hereby being incorporated by reference.

For the embodiment illustrated in FIG. 1, an expandable member or inflatable balloon 22 of the present invention is mounted near distal end 16. Inflatable balloon 22 is in fluid communication with lumen 18 via a fill hole or notch 24 (not shown) extending through tubular body 12 within balloon 22. Accordingly, balloon 22 may be inflated or deflated by the passage of fluid through notch 24.

Figure 2:
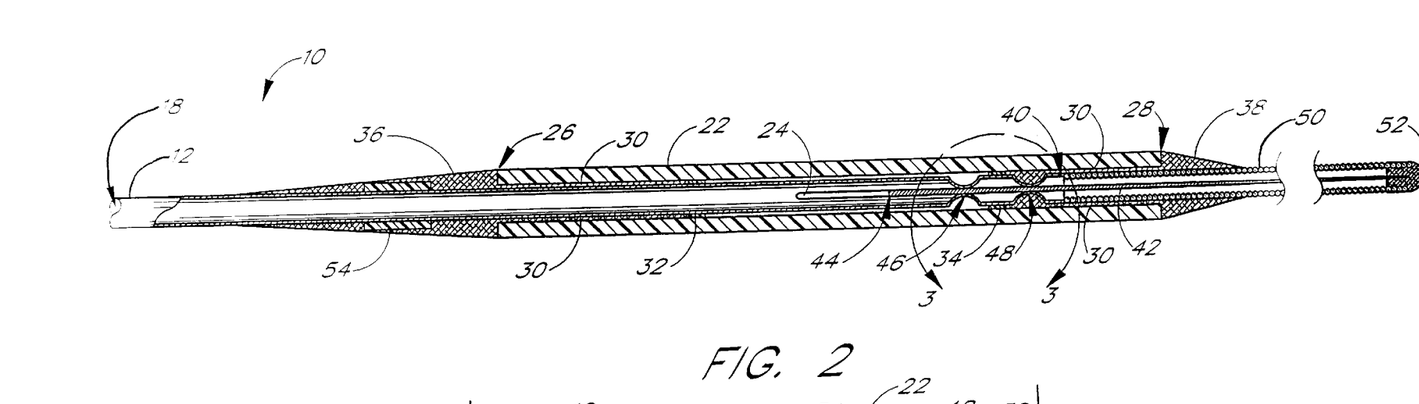
FIG. 2 is a longitudinal cross-sectional view of the distal end of the catheter having the pre-stretched balloon of the present invention.
Figure 3:
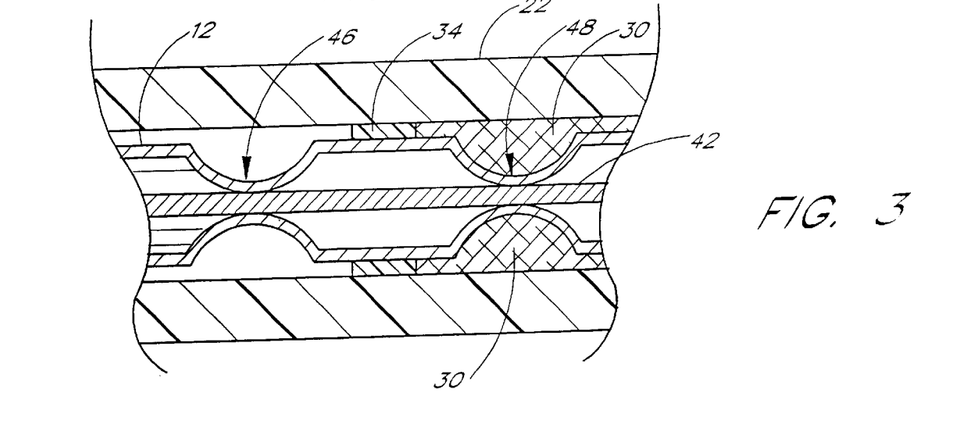
FIG. 3 is an enlarged cross-sectional view along area 3—3 of FIG. 2.

Referring to FIGS. 2 and 3, there is depicted a cross-sectional view of a distal section of the catheter 10. Notch 24 in FIG. 2 is shown on the back side of tubular body 12. Distal end 40 of tubular body 12 is provided with a core wire 42 surrounded by coil 50. Core wire 42 is preferably formed of a shape memory alloy, such as nitinol, but may also be formed of other materials, such as stainless steel. The core wire 42 and the coil 50 are formed into a subassembly prior to attachment to tubular body 12. Coil 50 is provided around the core wire 42, and is soldered at the distal tip of the core wire 42 forming a ball 52. Coil 50 is secured to the distal end 40 of tubular body 12 by suitable means such as soldering or brazing, or by an adhesive, as discussed below. One preferred adhesive type for connecting coil 50 to tubular body 12 is cyanoacrylate, although, as will be appreciated by those of skill in the art, other similar adhesives adopted to form metal to metal bonds may also be used. Coil 50 is formed of a suitable radiopaque material such as gold, platinum or a platinum alloy. Coil 50 can have a suitable outside diameter which corresponds to the outer diameter of tubular body 12, and can have a suitable length ranging from about 10 to about 50 mm. For example, where tubular body 12 has an outer diameter of 0.014 inches, and core wire 42 has a length of about 37 mm, coil 50 may have a length of about 35 mm.

Once the coil 50 is attached to the core wire 42 in the subassembly, a proximal end 44 of core wire 42 is inserted into a lumen 18 of tubular body 12 and is attached thereto. End 44 may be secured to lumen 18 by use of adhesives. Particularly preferred adhesives for attachment are cyanoacrylates of the type sold under the trade name Loctite. Other adhesives, such as metal to metal bond adhesives may also be used. Proximal end 44 of core wire 42 may be further secured within lumen 18 by crimping tubular body 12 such that the interior surface of tubular body 12 defining lumen 18 contacts proximal end 44 and firmly secures it within lumen 18. Tubular body 12 is crimped at two points 46 and 48 to secure proximal end 44 within lumen 18. Further details are disclosed in assignee's co-pending applications entitled CATHETER BALLOON CORE WIRE, application Ser. No. 08/813,024, filed March 6, 1997, and CORE WIRE WITH SHAPEABLE TIP Ser. No. 09/026357. filed Feb. 19, 1998 both of which are hereby incorporated by reference.

The balloon 22 preferably has a proximal portion 26 which is mounted to the tubular body 12, and a distal portion 28 which is partially mounted to the coil 50 as well as to the distal end 40 of tubular body 12. Together, the tubular body 12 and the core wire-coil subassembly comprise a catheter shaft to which the balloon 22 can be mounted. Balloon 22 may be secured by any means known to those of skill in the art, such as adhesives 30 or heat bonding. In one preferred embodiment, balloon 22 is a compliant balloon formed out of a material comprising a block copolymer of styrene-ethylene-butylene-styrene (SEBS), as described below. As described in more detail below, adhesive stops 32 and 34 are provided in the form of tubes surrounding the tubular body 12 within the balloon, preventing adhesive 30 from wicking into the balloon between the two stops. The adhesive stops 32 and 34 are preferably formed from a thermoset material such as polyimide, as described below. Tapers 36, 38 may be provided proximally and distally of balloon 22. A radiopaque marker 54 is located within taper 36 proximal of balloon 22.

Balloon Construction

Balloons of the present invention, such as balloon 22 shown in FIGS. 1, 2 and 3, may be formed out of any material used to manufacture inflatable catheter balloons, such as latex and silicone, or inelastic materials, such as polyethylene terephthalate, or out of a material comprising a block copolymer of styrene-ethylene-butylene-styrene (SEBS). It has been found that SEBS resins can be used to form catheter balloons with improved elasticity in comparison to other compliant balloon materials. Preferred SEBS resins for manufacture of balloons of the present invention may be purchased under the trade name C-FLEX, sold by Consolidated Polymer Technologies. In particular, the C-FLEX (TM) resin grade R70-050-000 has proven preferable for manufacture of balloons of the present invention. Other balloon materials having similar tensile strength, elongation, and hardness may also be used, such as C-FLEX (TM) resin grade R70-091-000 or other similar grade materials.

As a first step in the balloon formation process, the selected SEBS resin is extruded to form a tube which will subsequently be shaped into a balloon of the present invention. The resin may be extruded to form tubes having a variety of different internal and outer diameters, as can be readily appreciated by those of skill in the art. It is preferable, however, that the inner diameter of the extruded tubing be no more than about 120% greater and preferably no more than about 80% greater than the outer diameter of the catheter tubular body to which the finished balloon will be mounted. For example, where the outer diameter of tubular body 12 is about 0.014 inches, as is preferable for many hollow guidewire applications, the inner diameter before assembly of this extruded SEBS tubing is preferably from about 0.016 inches to about 0.030 inches, more preferably 0.020 inches to about 0.027 inches, and optimally about 0.025 inches. The outer diameter of the extruded SEBS tube is preferably about 0.035 inches to about 0.060 inches, more preferably 0.042 inches to about 0.058 inches, and optimally is 0.053 inches (for a 3.0 –4.0 mm balloon). Other balloon sizes will tend to require different dimensional parameters.

Any suitable one inch extrusion apparatus may be used to form the extruded SEBS tubes. For example, balloons of the present invention may be formed from tubing extruded on a 1" Harrel extruder, set to a draw down ratio of from about 1 to about 1.4, more preferably to a draw down ratio of about 1 to about 1.2.

It is important to monitor the extrusion process to ensure that the resulting tubing has substantially uniform inner and outer diameters along its length. In other words, uniform concentricity of the resulting extruded tube is very important. One important variable that needs to be monitored and controlled is the amount of tension which is applied to the tubing during the extrusion process. It is important not to apply too much tension, so that the tubing keeps proper dimensions along its length. For example, for extrusion of tubing having an inner diameter of about 0.025 inches and an outer diameter of about 0.053 inches, applied tension during extension preferably does not exceed 4 oz. The tubing preferably has a high tensile strength, because when the tubing is stretched, it gets thinner. A higher tensile strength allows the tubing to be made thinner without failure of the material to give the balloon a low profile.

Extrusion tension can be controlled by a variety of means, as is known to those of skill in the art. For example, extrusion tension can be controlled by using hand extrusion, by low tension pullers, by low tension winders, or by other means known to those of skill in the art.

The extruded SEBS tubing has an inner diameter much larger than the outer diameter of the catheter tubular body, such that the tubing may not be directly mounted to the tubular body to form a balloon. Accordingly, the inner diameter of the SEBS tubing must be reduced before the SEBS tube may be mounted to the catheter tubular body as a balloon.

Thus, one important step in forming balloons of the present invention involves reducing both the inner and outer diameter of the SEBS tubes by a pre-stretching process. Advantageously, the pre-stretching process not only reduces the inner and outer diameters such that the SEBS tubing may be mounted to a catheter tubular body as a balloon, but also results in a finished compliant balloon which exhibits reduced longitudinal expansion upon inflation. Indeed, it has been discovered that the pre-stretching process of the present invention is capable of reducing longitudinal expansion of finished SEBS balloons by from about 20% to about 50%.

The pre-stretching process generally comprises longitudinally stretching the extruded SEBS tube by at least 200%, such that substantially all lengthwise deformation of the SEBS tube occurs along a line parallel to the longitudinal axis of the SEBS tube. In other words, the tube is stretched lengthwise while controlling the stretching process variables to minimize curvature or other bends in the tube. Preferably, the extruded SEBS tube is stretched by at least 400%, more preferably by at least 600%, and optimally by at least 900%, such that the inner diameter of the SEBS tube decreases from its starting size to about 0.002–0.003 inches greater than the outer diameter of the catheter tubular body to which the extruded tube is to be mounted as a balloon. Furthermore, the pre-stretching process also preferably reduces the outer diameter of the SEBS tube from its starting size, to an outer diameter which is at least 15% smaller, more preferably 25% smaller, and optimally at least 30% smaller than the starting outer diameter size. For example, where the starting inner diameter of an extruded SEBS tube is about 0.025 inches, and the starting outer diameter of the tube is 0.053 inches, the tube may be stretched so that its length increases by about 600–700%, so that the resulting inner diameter of the tube is about 0.016 inches and the resulting outer diameter is about 0.035 inches. A stretched tube with these dimensions is preferably mounted to the embodiment of the tubular body 12 having an outer diameter of about 0.014 inches to form a balloon.

A particular advantage of manufacturing the SEBS tubing by the above-described pre-stretching process is that the balloon can be made with a lower profile than conventional balloons. Compliant balloons typically have a profile, measured by their cross-section, which is not low enough for use in applications such as coronary angioplasty or saphenous vein grafts. These procedures require insertion of the device into spaces on the order of about 2 to 4 mm. Although therapeutic catheters have employed balloons with such low profiles, these balloons are functionally different from compliant, elastomeric balloons. Therapeutic balloons are typically made of materials such as polyethylene terephthalate (PET) or nylon, which are molded in tube form and assume a shape of fixed dimension. Thus, they do not have the expansion characteristic desirable of compliant balloons. Furthermore, a therapeutic balloon can be folded for insertion into small spaces, but after inflation and deflation, the balloon cannot return to a folded form. The balloon that results from the above pre-stretching process is a compliant balloon which has a low profile which allows the balloon to be inserted in particularly small spaces.

As is readily appreciated by those of skill in the art, where the outer diameter of the tube is reduced more than the inner diameter, the thickness of the tube also decreases. Preferably the thickness is reduced by at least 10%, more preferably by at least 20%, and optimally by at least 30%. Greater reductions in thickness may also result from the pre-stretching process and still function in accordance with the present invention, depending upon the grade of SEBS resin and the stretching conditions used. The manner of adapting these different resin grades and stretching conditions will be apparent to those of skill in the art in view of the description heroin.

The pre-stretching process is preferably carried out at temperature which facilitates the stretching without contributing to any undesirable bending of the tube. For most grades of SEBS, temperatures of between about 0° to about 90° C. are preferred. Temperatures lower than this generally require the application of increased longitudinal force to carry out the stretching process, resulting in increased risk of nonuniform stretching or bending of the resulting tube. Moreover, at temperatures greater than about 90° C., the SEBS block copolymer used to form the tubing tends to soften considerably, such that gravitational force may introduce unwanted bend or curvature in the tube. Optimally, stretching is done at about 25–30° C.

The stretching rate also has an important effect on the properties of the resulting balloon. Preferably, the SEBS tubing is stretched at a rate of from about 0.5 cm per min to about 50 cm per minute, more preferably at a rate of less than 30 cm/min., and optimally is stretched at a rate of 10 cm inches per minute at room temperature. Stretching rates greater than the maximum amount may result in undesirable residual elongation. After the pre-stretching process is completed, the stretched SEBS tubing is preferably permitted to settle for a period of about 10–15 seconds, prior to removal from the stretching apparatus.

Balloon Centering

Once the pre-stretching process is complete, the stretched tubing is clamped on a fixture in order to create a balloon that is centered and will inflate in a uniform manner. The stretched tubing is heated along with the fixture to a temperature of about 60° to 120° C., and preferably about 100° C. The stretched tubing is stabilized at this temperature for about 15 minutes. After this stabilization step, the tubing and the fixture are cooled for about one hour at room temperature. Stabilization of the tubing by this process creates a balloon that will inflate in a uniform manner.

The stretched tubing is preferably cut to appropriate balloon length within two hours of the stretching, otherwise tube relaxation may occur which adversely affects the dimensions of the stretched tube. Cutting may be performed by any means known to those of skill in the art. One preferred cutting process comprises inserting a stainless steel mandrel into a polyimide tube, and then inserting the mandrel/polyimide tube combination into the lumen of the stretched SEBS tube. The stainless steel mandrel is then removed, leaving the polyimide tube within the stretched SEBS tube. The polyimide tube provides structural support to the SEBS tube during the cutting process, facilitating the formation of straight cut edges. For example, for a stretched SEBS tube having an inner diameter of about 0.016 inches and an outer diameter of about 0.035 inches, a stainless steel mandrel having an outer diameter of 0.013 inches is inserted into a polyimide tubing having an inner diameter of 0.0145 inches and an outer diameter of 0.0155 inches. The combination is then inserted into the stretched SEBS tube, and the stainless steel mandrel is removed. A standard cutting tool, such as a razor blade is then used to cut through the SEBS tubing and the polyimide tubing into segments having lengths of approximately 9 mm. After the cutting is completed, the polyimide tubing is removed.

Balloon Mounting

The stretched and cut pieces of SEBS tubing are bonded to catheter tubular bodies to form compliant inflatable balloons. Conventional balloon bonding techniques may be used to mount the SEBS tubing to catheter tubular bodies. Such techniques include adhesive bonding and heat bonding, as known to those of skill in the art. In one preferred embodiment where the catheter tubular body comprises nitinol, an adhesive stop is first prepared to prevent adhesive from bonding into the working length of the balloon. A thermoset material is preferred for the adhesive stop, and may comprise a pair polyimide tubes. These tubes are generally trimmed to a length of about 0.1 mm to 1 cm, more preferably trimmed to a length of between about 0.2 and 0.5 mm, and even more preferably have a length of about 0.25 mm. These tubes preferably have an outer diameter close to the size of the inner diameter of the balloon. Thus, for a tubular body 12 with an outer diameter of about 0.014 inches, the inner diameter of the adhesive stops 32 and 34 shown in FIGS. 2 and 3 is about 0.0142 inches. The wall thickness of stops 32 and 34 is about 0.002 inches, such that the outer diameter of the stops is about 0.0182 inches.

The two polyimide tubes are primed with 7701 LOCTITE or similar material on their inner surfaces. A first polyimide tube 32 is slid over the core wire-coil subassembly and onto the tubular body 12. A primer is then applied to the inner surface of each end of the SEBS tube to improve the bonding of the SEBS tube to nitinol. One suitable primer found useful for the priming step is 7701 LOCTITE, sold by Loctite Corp. However, as will be appreciated by those of skill in the art, other primers may also be used. The primer is preferably applied only to the inner surface of the SEBS tube at its ends, and more preferably, each end inner surface is primed for a distance of about 2 mm extending inward.

The primed tubing is slid over the catheter tubular body to the appropriate balloon position, such as over a fill hole or notch 24 in communication with inflation lumen 18, as shown in FIG. 2. In a preferred embodiment, the distal end 28 of the SEBS tubing is positioned partially on tubular body 12, and partially on coil 50. The second polyimide tube 34 is then slid over the core wire-coil subassembly. The polyimide tubes 32 and 34 are positioned on the tubular body 12 and within balloon 22 by the use of a polyimide positioning tube (not shown). For positioning the distal tube 34, the positioning tube slides over the core wire-coil subassembly to gently push the tube 34 underneath the balloon 22 and into the appropriate position. For positioning the proximal tube 32, the positioning tube is cut into a C-shape for attachment to tubular body 12 at a location proximal of balloon 22, thereby eliminating the need to slide the positioning tube all the way from the proximal end of tubular body 12. The positioning tube then gently pushes tube 32 underneath the balloon and into an appropriate position.

The precise positions of the polyimide tubes 32 and 34 will depend on the desired dimensions of the balloon and the desired working length. As defined by the distance between the inside edges of the polyimide tubes, this working length is preferably in the range of about 2–8 mm, and more preferably, about 5 mm. For example, if a 9 mm SEBS tube is bonded to a catheter tubular body along 2 mm at each end of the SEBS tube, adhesive stops are placed slightly inward of the 2 mm mark, so that about 5 mm of the SEBS tube is not bonded to the tubular body, and may function as a balloon. For this embodiment, the first tube 32 is preferably located about 6 mm from the distal end 28 of tubular body 12, and the second tube 34 is preferably located about I mm from the distal end 28, and between the crimps 46 and 48.

The SEBS tubing is then mounted to the tubular body 12 and the coil 50 to form a fluid tight seal. When using the LOCTITE 4011 adhesive, however, it is important to control the humidity of the surrounding environment, such that the humidity is maintained at at least 35% to 40%. As shown in FIG. 2, adhesive 30 is preferably applied at the proximal and distal ends 26 and 28, respectively, of the balloon 22 by the use of a syringe and a dispensing needle. As shown in FIGS. 2 and 3, while adhesive bonding is taking place, the adhesive 30 wicks to the balloon 22 from the proximal and distal ends 26 and 28, respectively, inward. As this occurs, the polyimide tubes 32 and 34 will eventually stop the adhesive 30 from wicking into the working area. This ensures that for a catheter with thermoset tubings spaced 5 mm apart, the working length of the balloon will be maintained at 5 mm. This control over the working length also contributes to uniform inflation of the balloon 22. Furthermore, as the adhesive 30 wicks into the balloon from distal end 28 toward tube 34, the adhesive seals the coil 50 to the distal end 40 of tubular body 12.

After the SEBS tube has been bonded to the catheter tubular body to form a balloon, and the adhesive has set, tapers 36 and 38 are preferably formed on the balloon to facilitate unhindered movement within a patient. Taper 36 preferably covers a distal marker 54, as described in the above-referenced SHAFT FOR MEDICAL CATHETERS, application Ser. No. 09/026105, filed on the same day as the present application. Tapers may be added by conventional means known to those of skill in the art, such as adhesive bonding of the tapered parts separately to the catheter after the balloon has been attached. Alternately, tapers can be formed by adhesives which are applied to the balloon. In addition, it is possible to mold the balloon with a taper and then attach it.

Although the adhesive stop has been described in the form of a pair of tubes, other shapes and configurations would also suffice to prevent adhesive wicking into the balloon area. For instance, the adhesive stop can take the form of one polyimide tube extending through the working length of the balloon with a notch in the middle to provide fluid communication between the lumen 18 and the balloon 22. In such a case, the working length of the balloon is approximately defined by the distance between the proximal and distal ends of the polyimide tube.

Furthermore, it should be appreciated that although the preferred embodiment has been described in terms of the SEBS tubing and the polyimide tubes 32, 34 being bonded to tubular body 12, the present invention should not be limited to this embodiment. More generally, the SEBS tubing and polyimide tubes may be bonded to an elongate catheter shaft. This catheter shaft may be solid or tubular, and may comprise a hypotube such as tubular body 12 alone, or may comprise the tubular body 12 in combination with other elements, such as the core wire-coil subassembly as described above.

Inflation Syringe and Balloon Sizing System

The balloon manufacturing method described above allows for simplification of the balloon sizing and inflation volume system used by the physician. Prior systems required a broad range of inflation devices to be used in combination with various sizes of balloons. For example, balloon diameters of 3.0 mm, 3.5 mm, 4.0 mm, 4.5 mm, 5.0 mm, 5.5 mm, and 6.0 mm are common. Thus, previous technology could require as many as 6 different balloon diameters and 6 different inflation devices each with a specific volume, to inflate the balloons. Further details are provided in copending application titled SYRINGE AND METHOD FOR INFLATING LOW VOLUME CATHETER BALLOONS application Ser. No. 09/025991, filed Feb. 19, 1998, the entirety of which is incorporated by reference.

With the present balloon catheters, however, this system can be simplified. A single inflation device (e.g., a syringe) may be used to inflate a single compliant balloon having diameters of from 3.0 to 6.0 mm. For example, a single extruded SEBS tube having an outer diameter of 0.045 inches, an inner diameter of approximately 0.017–0.018 inches, and length of 10 mm, after stretching, can be sealed on the catheter surrounding the inflation hole as described above. Approximately 2.5 mm of the tube is sealed onto the catheter body. This leaves approximately 5.0 mm of length which is able to expand upon inflation. As will be understood by those of ordinary skill in the art, as the balloon expands, its central portion will come into direct contact with the vessel wall, while the ends of the balloon will taper down to the point where the balloon is sealed onto the catheter. The shape that the balloon assumes is somewhat like a football with elongated, flattened sides, as the balloon seals against the walls of the vessel. Depending upon the amount of fluid used to inflate the balloon, the balloon will expand until lengths of from about 3.0 to about 6.0 mm come into direct contact with the interior of the vessel. This will provide satisfactory sealing, occlusion, anchoring and the like, when properly inflated as set forth in the chart below. Sealing can be partial or complete. Thus, a single balloon provides a useful length ranging from about 3.0 to about 6.0 mm.

Alternatively, a system having two balloon sizes and a single syringe may be used. One balloon, able to expand until approximately 3.0 to 4.0 mm contacts the interior of the vessel, is used for smaller occlusions. A second balloon, which expands to approximately 4.25 to 6.0 mm useful length is used for large occlusions. A single syringe is used to provide inflation fluid. If desired, the syringe may be marked with indicia along its barrel to assist the physician during inflation of the balloon. Thus, the syringe may be marked, for example, with the volumes sufficient to inflate balloons having diameters as indicated in the following chart:

| Balloon Size | Syringe Volume |
| --- | --- |
| 3.0 mm | 0.07 cc |
| 3.5 mm | 0.07 cc |
| 4.0 mm | 0.10 cc |
| 4.5 mm | 0.125 cc |
| 5.0 mm | 0.15 cc |
| 5.5 mm | 0.19 cc |
| 6.0 mm | 0.225 cc |

It will be appreciated that certain variations of the present invention may suggest themselves to those skilled in the art. The foregoing detailed description is to be clearly understood as given by way of illustration, the spirit and scope of this invention being limited solely by the appended claims.

What is claimed is:

1. An inflatable balloon catheter, comprising:

an elongate tubular body having proximal and distal ends;

a lumen extending through the tubular body from the proximal end to the distal end;

an inflatable balloon with an interior volume in fluid communication with the lumen, the balloon having proximal and distal ends both of which are bonded concentrically to the tubular body by an adhesive, the balloon having a working area within the interior volume;

an opening in a side wall of the elongate tubular body positioned at least partially between the proximal and distal ends of the balloon for communicating fluids from the lumen to the interior volume of the balloon; and a pair of adhesive stops located on the elongate tubular body and on either side of the opening and within the interior volume of the balloon to prevent the adhesive from wicking into the working area of the balloon.

2. The catheter of claim 1 wherein the adhesive stops are tubular.

3. The catheter of claim 1 wherein the adhesive stops are made of a thermoset material.

4. The catheter of claim 1 wherein the adhesive stops are made of a polyimide.

5. The catheter of claim 1 wherein the adhesive stops each have a length of about 0.25 mm.

6. The catheter of claim 1 wherein the distance between the adhesive stops is about 4 mm.

7. A balloon catheter, comprising:

an elongate catheter shaft;

a balloon having an interior volume and proximal and distal ends, the balloon being bonded concentrically at its proximal and distal ends to the catheter shaft by an adhesive, wherein both the proximal and distal ends of the balloon are bonded to the catheter shaft;

an opening in a side wall of the elongate catheter shaft positioned at least partially between the proximal and distal ends of the balloon for communicating fluids to the balloon; and an adhesive stop located on the elongate catheter shaft within the interior volume of the balloon on at least one side of the opening to prevent the adhesive from wicking into the balloon past the location of the adhesive stop.

8. The balloon catheter of claim 7, wherein the catheter shaft comprises an elongate tubular body having proximal and distal ends and a lumen extending through the tubular body from the proximal end to the distal end, the interior volume of the balloon being in fluid communication with the lumen.

9. The balloon catheter of claim 8, wherein the catheter shaft further comprises:

a core wire attached to the distal end of the tubular body; and a coil surrounding the core wire.

10. The balloon catheter of claim 9, wherein the distal end of the balloon is bonded at least partially to the coil.

11. The catheter of claim, 1, wherein the inflatable balloon is made from a longitudinally pre-stretched elastomeric material.

12. The catheter of claim 11, wherein the inflatable balloon is made from a longitudinally pre-stretched styrene-ethylene-butylene-styrene material.

13. A medical catheter, comprising:

an elongate body having a proximal end and a distal end;

an expandable member mounted at the distal end of the elongate body, the expandable member having a proximal end and a distal end that are both mounted to the elongate body; and a first tube and a second tube spaced apart along the elongate body near the distal end of the elongate body;

wherein the expandable member is mounted to the elongate body over the first tube and the second tube, and the expandable member adheres to the elongate body from its proximal end up to about the location of the first tube and from its distal end up to about the location of the second tube.

14. The catheter of claim 13, wherein the expandable member is an inflatable balloon.

15. The catheter of claim 14, wherein the balloon is a longitudinally pre-stretched elastomeric material.

16. The catheter of claim 13, wherein the elongate body is tubular having a lumen extending therethrough.

17. The catheter of claim 16, further comprising a core wire extending into the distal end of the lumen.

18. The catheter of claim 17, further comprising a coil surrounding the core wire extending from the distal end of the elongate body.

19. The catheter of claim 18, wherein the expandable member is adhered near its distal end to both the distal end of the elongate body and to the coil.

20. The catheter of claim 13, wherein the expandable member adheres to the elongate body with an adhesive.

21. The catheter of claim 20, wherein the adhesive is a cyanoacrylate.

* * * * *